US010850267B2

(12) United States Patent
Xiang et al.

(10) Patent No.: US 10,850,267 B2
(45) Date of Patent: Dec. 1, 2020

(54) PREPARATION METHOD FOR METAL-MODIFIED SAPO MOLECULAR SIEVE

(71) Applicant: Dalian Institute of Chemical Physics, Chinese Academy of Sciences, Shahekou Dalian (CN)

(72) Inventors: Xiao Xiang, Shahekou Dalian (CN); Peng Tian, Shahekou Dalian (CN); Zhongmin Liu, Shahekou Dalian (CN); Yue Yang, Shahekou Dalian (CN); Lin Liu, Shahekou Dalian (CN); Miao Yang, Shahekou Dalian (CN); Hongyi Yang, Shahekou Dalian (CN); Shiyun Sang, Shahekou Dalian (CN); Yanli He, Shahekou Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 15/547,264

(22) PCT Filed: Jan. 30, 2015

(86) PCT No.: PCT/CN2015/071960
§ 371 (c)(1),
(2) Date: Jul. 28, 2017

(87) PCT Pub. No.: WO2016/119222
PCT Pub. Date: Aug. 4, 2016

(65) Prior Publication Data
US 2018/0021763 A1 Jan. 25, 2018

(51) Int. Cl.
*C01B 39/54* (2006.01)
*B01J 29/85* (2006.01)
*C01B 39/02* (2006.01)
*C01B 37/08* (2006.01)
*B01D 53/86* (2006.01)
*B01J 37/00* (2006.01)
*B01J 37/06* (2006.01)
*B01J 37/08* (2006.01)
*B01J 37/30* (2006.01)
*C07C 1/20* (2006.01)

(52) U.S. Cl.
CPC .......... *B01J 29/85* (2013.01); *B01D 53/8628* (2013.01); *B01J 37/0018* (2013.01); *B01J 37/06* (2013.01); *B01J 37/08* (2013.01); *B01J 37/30* (2013.01); *C01B 37/08* (2013.01); *C01B 39/026* (2013.01); *C01B 39/54* (2013.01); *C07C 1/20* (2013.01); *B01D 2255/50* (2013.01); *B01D 2258/06* (2013.01); *B01J 2229/183* (2013.01); *C07C 2529/85* (2013.01)

(58) Field of Classification Search
CPC ........ C01B 39/54; C01B 39/026; B01J 29/85; B01J 37/30
See application file for complete search history.

(56) References Cited

U.S. PATENT DOCUMENTS

| 4,440,871 A * | 4/1984 | Lok ........................ B01J 20/18 502/214 |
| 5,962,762 A * | 10/1999 | Sun ........................ B01J 29/85 585/640 |
| 2003/0187313 A1* | 10/2003 | Wang ...................... B01J 29/85 585/634 |

FOREIGN PATENT DOCUMENTS

| CN | 103008002 A * | 4/2013 | ............. B01J 29/85 |
| CN | 103008002 A | 4/2013 | |
| EP | 2269733 A1 | 1/2011 | |
| WO | 2009/099937 A1 | 8/2009 | |
| WO | 2013/159828 A1 | 10/2013 | |

OTHER PUBLICATIONS

Yu et al, "The effect of various templates on the NH3-SCR activities over Cu-SAPO-34 catalysts", Chemical Engineering Journal, (Jan. 10, 2014), pp. 159-168. (Year: 2014).*
Feng Gao et al., "Synthesis and evaluation of Cu/SAPO-34 catalysts for NH 3-SCR 2: Solid-state ion exchange and one-pot synthesis", Applied Catalysis B: Environmental, Aug. 19, 2014, pp. 501 to 514, vol. 162, Amsterdam, Netherlands.
"European Search Report and Written Opinion in Application No. 15879430.5", dated Jul. 3, 2018.
Xiang et al., "Direct Cu2+ ion-exchanged into as-synthesized SAPO-34 and its catalytic application in the selective catalytic reduction of NO with NH3", RSC Advances, Jan. 20, 2016, pp. 12544-12552, vol. 6, The Royal Society of Chemistry.
Gao et al., "Synthesis and Evaluation of Cu-SAPO-34 Catalysts for Ammonia Selective Catalytic Reduction. 1. Aqueous Solution Ion Exchange", ACS Catalysis, Aug. 1, 2013, pp. 2083-2093, American Chemical Society.
Follens, Lana, "Communication pursuant to Article 94(3) EPC in European Application No. 15 879 430.5", Feb. 12, 2020, European Patent Office.

(Continued)

*Primary Examiner* — David M Brunsman
(74) *Attorney, Agent, or Firm* — Edwin A. Sisson, Attorney at Law, LLC; Jeffrey J. Banyas

(57) ABSTRACT

A preparation method for a metal-modified SAPO molecular sieve is disclosed, characterized in adding a raw powder of the SAPO molecular sieve to a solution containing metal ions for performing ion exchange, and then washing and drying the obtained solid after ion exchange, so as to obtain the metal-modified SAPO molecular sieve. The metal-modified SAPO molecular sieve prepared has a relatively high degree of crystallinity, and the metal elements occupy the ionic positions in the channels and/or cages of the SAPO molecular sieve, and the metal-modified SAPO molecular sieve shows excellent catalytic performance in the catalytic reaction.

6 Claims, 1 Drawing Sheet

(56) References Cited

OTHER PUBLICATIONS

Tan Yuxin et al., "Study on Hydrothermal Stability of Automobile Exhaust Gas Ag-SAPO-34 Catalyst under Lean-burn Condition", Shanghai Environmental Sciences, Oct. 31, 2001, pp. 474-476, vol. 20, No. 10.

Xu, Hui, "International Search Report, International Application No. PCT/CN2015/071960", dated Oct. 29, 2015.

* cited by examiner

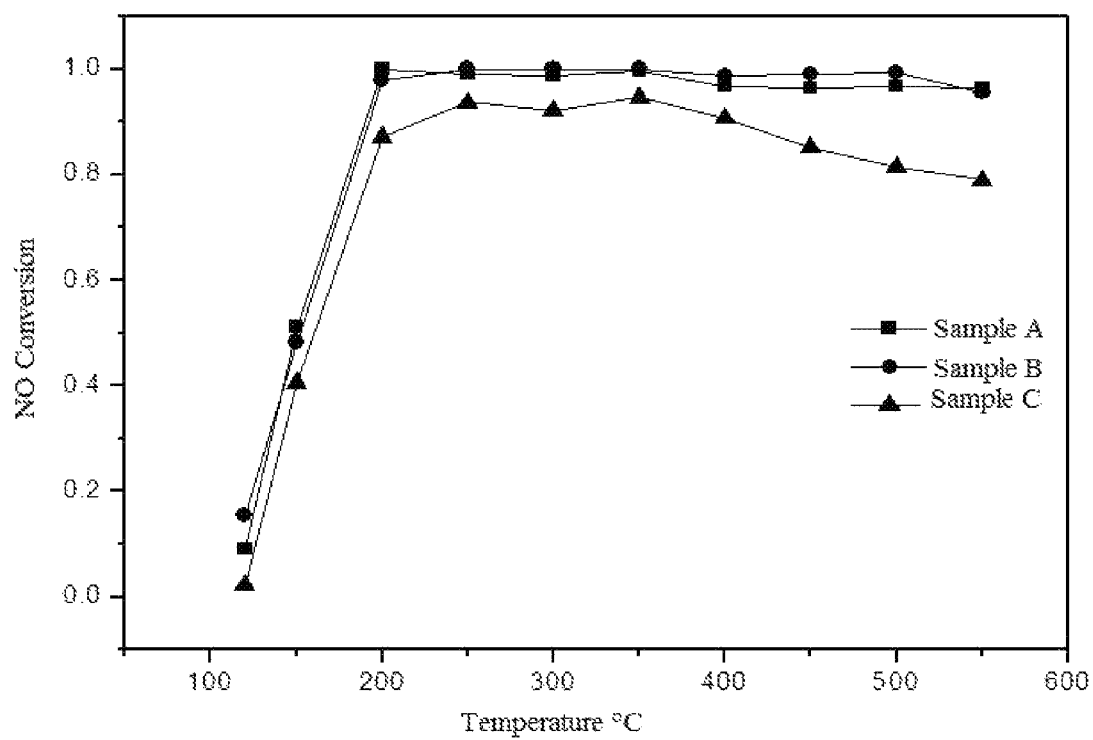

PREPARATION METHOD FOR METAL-MODIFIED SAPO MOLECULAR SIEVE

PRIORITIES AND CROSS REFERENCES

This Application is a 371 filing of PCT/CN2015/071960 filed on 30 Jan. 2015.

TECHNICAL FIELD

The present application relates to a preparation method for metal-modified SAPO molecular sieves, and belongs to the field of porous materials.

BACKGROUND

Aluminum phosphate molecular sieves and heteroatom substituted aluminum phosphate molecular sieves are the research hotspots in materials science and catalysis field. In particular, SAPO-n (n represents the type) series of silicoaluminophosphate molecular sieves have a framework composed of $PO_2^+$, $AlO_2^-$ and $SiO_2$ tetrahedrons, in which Si atoms, instead of Al atoms, enter into the framework of neutral aluminum phosphate molecular sieves, leading to the formation of negative charges in the framework. Depending on synthesis conditions and Si contents, SAPO molecular sieves exhibit moderate to strong protonic acidity. In addition, many SAPO molecular sieves have a regular channel structure and good thermal stability and hydrothermal stability. Therefore, such materials have been widely used as adsorbents, catalysts and catalyst carriers, and are highly valued in academic and industrial world at home and abroad.

After modification by ion exchange, SAPO molecular sieves loaded with an active metal have broad application prospects. For example, Cu-SAPO-34 prepared by ion exchange can be used as a catalyst for a reaction selectively removing $NO_x$; and in a reaction converting methanol to olefins, the introduction of Ce ions into SAPO-34 by ion exchange can increase the selectivity for ethylene and the lifetime of the SAPO-34 catalyst.

In order to achieve the objective that metal ions are located at ion sites of a SAPO molecular sieve, rather than covering the outer surface or present in a form of metal oxide on the molecular sieve, a basic process that has been used for decades is as follows: (1) calcining a raw powder of the molecular sieve to remove organic templating agents contained therein, which renders the channels of the molecular sieve unblocked; (2) adding the calcined molecular sieve to an aqueous solution of ammonium nitrate to obtain a ammonium type molecular sieve by ion exchange; and (3) adding the ammonium type molecular sieve to an aqueous solution containing metal ions, in which $NH_4^+$ ions are exchanged with metal ions, so as to obtain a metal-modified SAPO molecular sieve. The preparation process above is cumbersome, and moreover the framework structure of a molecular sieve will be damaged to a certain extent during repeated ion exchange, due to poor low-temperature hydrothermal stability of the SAPO molecular sieve. It may lead to collapse of the framework structure of the molecular sieve, especially when the aqueous solution containing metal ions is acidic.

SUMMARY OF THE INVENTION

According to an aspect of the present application, there is provided a preparation method for a metal-modified SAPO molecular sieve. Compared with a traditional method of "calcining molecular sieve raw powder-ammonium exchange-metal ion exchange", in the method according to the present application, steps of "calcining molecular sieve raw powder" and "ammonium exchange" are omitted. It avoids damage to the framework structure of SAPO molecular sieves caused by the metal modification process, and simultaneously provides a metal-modified molecular sieve in which metal ions are located at ion sites in channels and/or cages to balance the negative charges in the framework.

The preparation method for a metal-modified SAPO molecular sieve comprises at least the following steps: adding SAPO molecular sieve raw powder to a solution containing metal ions and performing ion exchange, and then washing and drying the obtained solid after the ion exchange, so as to obtain the metal-modified SAPO molecular sieve.

As a preferred embodiment, the preparation method for a metal-modified SAPO molecular sieve is characterized by adding SAPO molecular sieve raw powder to a solution containing metal ions and performing ion exchange, and then washing and drying the obtained solid after ion exchange, so as to obtain the metal-modified SAPO molecular sieve.

The preparation method for a metal-modified SAPO molecular sieve is as follows:

(1) dissolving a metal salt in water and/or an organic solvent to obtain a solution containing metal ions;

(2) adding SAPO molecular sieve raw powder to the solution containing metal ions obtained in step (1) at a certain solid-to-liquid ratio and performing ion exchange at a certain temperature; and (3) after completion of the ion exchange, performing solid-liquid separation and drying the obtained solid at a temperature range from 50° C. to 120° C., so as to obtain the metal-modified SAPO molecular sieve.

The metal salt is an inorganic metal salt and/or an organic metal salt.

Preferably, the organic solvent is at least one selected from water, methanol, ethanol.

Preferably, the SAPO molecular sieve raw powder is at least one selected from SAPO-34 molecular sieve raw powder, SAPO-35 molecular sieve raw powder, SAPO-56 molecular sieve raw powder, SAPO-18 molecular sieve raw powder, SAPO-5 molecular sieve raw powder, SAPO-11 molecular sieve raw powder, DNL-6 molecular sieve raw powder.

Preferably, the metal ion is at least one selected from Group IA metal ions, Group IIA metal ions, Group IIIA metal ions, Group VA metal ions, Group IVB metal ions, Group VB metal ions, Group VIIB metal ions, Group VIII metal ions, Group IB metal ions, Group IIB metal ions, lanthanide metal ions.

Preferably, the metal ion is at least one selected from copper ions, iron ions, lanthanum ions, cerium ions, cobalt ions, nickel ions, zinc ions, manganese ions, magnesium ions, vanadium ions, zirconium ions, barium ions, platinum ions, gold ions, palladium ions, silver ions, rhodium ions, ruthenium ions, aluminum ions, bismuth ions, gallium ions, calcium ions, strontium ions, lithium ions, sodium ions, potassium ions, rubidium ions, cesium ions. More preferably, the metal ion is at least one selected from copper ions, cerium ions, nickel ions, manganese ions, strontium ions. The metal ion includes a variety of valence states. For example, copper ions are $Cu^+$ and/or $Cu^{2+}$, and iron ions are $Fe^{2+}$ and/or $Fe^{3+}$, and the like.

The SAPO molecular sieve raw powder is synthesized by a hydrothermal or solvothermal method. The general process is that an initial gel mixture containing a silicon source, an aluminum source, a phosphorous source, an organic templating agent, and water and/or an organic solvent is crystallized at a certain crystallization temperature for a period of time, and after the crystallization is finished, the obtained solid is separated, washed and dried at a drying temperature no more than 300° C., so as to obtain the SAPO molecular sieve raw powder.

Preferably, an organic templating agent is used in the synthesis of the SAPO molecular sieve raw powder.

Preferably, the organic templating agent used in the synthesis of SAPO-34 molecular sieve raw powder contains at least one organic amine compound with no more than 8 carbon atoms.

Preferably, the organic templating agent used in the synthesis of SAPO-18 molecular sieve raw powder contains at least one organic amine compound with no more than 8 carbon atoms.

Preferably, the organic templating agent used in the synthesis of SAPO-56 molecular sieve raw powder contains at least one organic amine compound with no more than 10 carbon atoms.

Preferably, the organic templating agent used in the synthesis of SAPO-5 molecular sieve raw powder contains at least one organic amine compound with no more than 9 carbon atoms.

Preferably, the organic templating agent used in the synthesis of SAPO-11 molecular sieve raw powder contains at least one organic amine compound with no more than 8 carbon atoms.

Preferably, the organic templating agent used in the synthesis of SAPO-35 molecular sieve raw powder contains at least one organic amine compound with no more than 8 carbon atoms.

Preferably, the organic templating agent used in the synthesis of DNL-6 molecular sieve raw powder contains at least one organic amine compound with no more than 8 carbon atoms.

More preferably, an organic templating agent is used in the synthesis of the SAPO molecular sieve raw powder, and the organic templating agent contains at least one organic amine compound with no more than 10 carbon atoms. Still more preferably, an organic templating agent is used in the synthesis of the SAPO molecular sieve raw powder, and the organic templating agent contains at least one selected from diethylamine, triethylamine, N,N-diisopropylethylamine, hexamethyleneimine, N,N,N,N-tetramethyl-1,6-hexanediamine, tetrabutylammonium hydroxide, di-n-propylamine.

Preferably, the mass ratio of the SAPO molecular sieve raw powder to the solution containing metal ions (SAPO molecular sieve raw powder: solution containing metal ions) is in a range from 1:3 to 1:100. More preferably, the upper limit of the mass ratio range of the SAPO molecular sieve raw powder to the solution containing metal ions is selected from 1:8, 1:10, 1:20, 1:30, 1:40, 1:45; and a lower limit of the mass ratio range of the SAPO molecular sieve raw powder to the solution containing metal ions is selected from 1:100, 1:90, 1:80, 1:70, 1:60, 1:50. Still more preferably, the mass ratio of the SAPO molecular sieve raw powder to the solution containing metal ions (SAPO molecular sieve raw powder: solution containing metal ions) is in a range from 1:8 to 1:100.

Preferably, the metal ion concentration in the solution containing metal ions is in a range from 0.002 mol/L to 1 mol/L. More preferably, the upper limit of the metal ion concentration range is selected from 1 mol/L, 0.9 mol/L, 0.8 mol/L, 0.7 mol/L, 0.6 mol/L, 0.5 mol/L; and the lower limit of the metal ion concentration range is selected from 0.002 mol/L, 0.01 mol/L, 0.02 mol/L, 0.1 mol/L, 0.2 mol/L, 0.3 mol/L, 0.4 mol/L. Still more preferably, the metal ion concentration in the solution containing metal ions is in a range from 0.005 mol/L to 0.5 mol/L.

Preferably, the ion exchange temperature is in a range from −10° C. to 150° C. More preferably, the upper limit of the temperature range for ion exchange is selected from 150° C., 140° C., 130° C., 120° C., 100° C., 90° C., 85° C.; and the lower limit of the temperature range for ion exchange is selected from −10° C., −5° C., 0° C., 10° C., 30° C., 50° C. Still more preferably, the ion exchange temperature is in a range from 40° C. to 90° C.

Preferably, the ion exchange time is in a range from 0.5 h to 60 h. More preferably, the upper limit of the ion exchange time range is selected from 60 h, 50 h, 40 h, 30 h, 20 h, 10 h; and the lower limit of the ion exchange time range is selected from 0.5 h, 1 h, 2 h, 3 h, 4 h, 6 h, 8 h, 9 h. Still more preferably, the ion exchange time is in a range from 0.5 h to 10 h.

Preferably, the ion exchange temperature is in a range from −10° C. to 150° C. and the ion exchange time is in a range from 0.5 h to 60 h. More preferably, the ion exchange temperature is in a range from 40° C. to 90° C. and the ion exchange time is in a range from 0.5 h to 10 h.

As a preferred embodiment, the obtained solid is washed, dried and calcined at a temperature no less than 600° C., to obtain the metal-modified SAPO molecular sieve. The organic substances present in the channels and cages of the molecular sieve will limit the mass transfer by diffusion to a certain extent during the ion exchange, which may lead to the uneven distribution of metal ions in channels and cages of the SAPO molecular sieve. High temperature calcining after ion exchange of metal ions into SAPO raw powder can promote the dispersion of metal ions in the molecular sieve grains, thereby obtaining the samples with more uniform distribution of metal ions.

According to yet another aspect of the present application, there is provided a catalyst for conversion reaction of an oxygenate, which is obtained by calcining a metal-modified SAPO molecular sieve in air at a temperature range from 400° C. to 700° C., and the SAPO molecular sieve is prepared according to any one of the above methods. Preferably, the calcining temperature is in a range from 600° C. to 700° C.

According to yet another aspect of the present application, there is provided a catalyst for oxidation reaction of a hydrocarbon, which is obtained by calcining a metal-modified SAPO molecular sieve in air at a temperature range from 400° C. to 700° C., and the SAPO molecular sieve is prepared according to any one of the above methods. Preferably, the calcining temperature is in a range from 600° C. to 700° C.

According to yet another aspect of the present application, there is provided a catalyst for $NO_x$ removing reaction, which is obtained by calcining a metal-modified SAPO molecular sieve in air at a temperature range from 400° C. to 700° C., and the SAPO molecular sieve is prepared according to any one of the above methods. Preferably, the calcining temperature is in a range from 600° C. to 700° C.

As used in the present application, the term "molecular sieve raw powder" refers to a sample that has not been calcined at a temperate above 300° C. The organic templating agent and a small amount of water are contained in channels and cages of the molecular sieve raw powder.

As used in the present application, the term "DNL-6" refers to a SAPO molecular sieve with a RHO structure.

As used in the present application, the term "$NO_x$" refers to a nitrogen oxide, including multifarious compounds consisting of nitrogen and oxygen and mixtures formed by any combination of these compounds, such as nitrous oxide ($N_2O$), nitric oxide (NO), nitrogen dioxide ($NO_2$), dinitrogen trioxide ($N_2O_3$), dinitrogen tetroxide ($N_2O_4$), dinitrogen pentoxide ($N_2O_5$) and the like.

The benefits brought by the technical solution of the present application includes at least:

(1) Compared with traditional methods, in the preparation method for a metal-modified SAPO molecular sieve provided by the present application, steps of "calcining molecular sieve raw powder" and "ammonium exchange" are omitted, which may reduce discharge of waste liquid and simultaneously save working hours and improve efficiency.

(2) The preparation method for a metal-modified SAPO molecular sieve provided by the present application greatly reduces the damage to molecular sieve structure during the ion exchange process, and the prepared metal-modified SAPO molecular sieve has a high degree of crystallinity (3) The metal-modified SAPO molecular sieve, prepared by the preparation method for a metal-modified SAPO molecular sieve provided by the present application, exhibits excellent catalytic performance in the catalytic reactions.

BRIEF DESCRIPTION OF THE DRAWINGS

FIG. 1 shows the NO conversion on Sample A, Sample B, and Sample C in Example 7.

DETAILED DESCRIPTION OF THE EMBODIMENT

The present application will be further described in combination with examples. It should be understood that these examples are merely illustrative of the present application and are not to limit the scope of the present application.

Unless otherwise specified, the test conditions used in the present application were as follows: X-ray powder diffraction phase analysis (XRD) was performed using X'Pert PRO X-ray diffractometer (PANalytical B.V., Netherlands) with a Cu target, a Kα radiation source (λ=0.15418 nm), a voltage of 40 KV and a current of 40 mA was used.

Thermogravimetric analysis was performed using SDT Q600 analyzer (TA INSTRUMENTS, USA). $H_2$-TPR analysis was performed using Autochem 2920 chemical adsorption apparatus (Micromeritics, USA).

Elemental composition was measured using Magix 2424 X-ray fluorescence analyzer (XRF) from Philips.

CHN elemental analysis was performed using German-made Vario EL Cube element analyzer.

Electron paramagnetic resonance (EPR) characterization was performed using Bruker A200 instrument.

The elemental analysis by energy dispersive X-ray spectroscopy (EDX) was performed using Hitachi SU8020 electron microscope with a Horiba X-max probe.

Example 1 Preparation of Molecular Sieve Raw Powder

Preparation of SAPO-34 Molecular Sieve Raw Powder, O34-1:

According to the method described in [Literature 1], a sample was prepared using diethylamine (abbreviated as DEA) as the organic templating agent, and after being dried at a temperature of 120° C., a SAPO-34 molecular sieve raw powder was obtained and denoted as Sample O34-1.

[Literature 1]: *Microporous and Mesoporous Materials*, 2008, 114 (1-3), 416-423.

Preparation of SAPO-34 Molecular Sieve Raw Powder, O34-2:

According to the method described in [Literature 2], a sample was prepared using triethylamine (abbreviated as TEA) as the organic templating agent, and after being dried at a temperature of 120° C., a SAPO-34 molecular sieve raw powder was obtained and denoted as Sample O34-2.

[Literature 2]: *Microporous and Mesoporous Materials*, 2002, 53 (1-3), 97-103.

Preparation of SAPO-18 Molecular Sieve Raw Powder, O18-1:

According to the method described in [Literature 3], a sample was prepared using N,N-diisopropylethylamineas the organic templating agent, and after being dried at a temperature of 120° C., a SAPO-18 molecular sieve raw powder was obtained and denoted as Sample O18-1.

[Literature 3]: *Journal of Physical Chemistry*, 1994, 98 (40), 10216-10224.

Preparation of DNL-6 Molecular Sieve Raw Powder, O6-1:

According to the method described in [Literature 4], a sample was prepared using diethylamine as the organic templating agent, and after being dried at a temperature of 120° C., a the DNL-6 molecular sieve raw powder was obtained and denoted as Sample O6-1.

[Literature 4]: *Microporous and Mesoporous Materials*, 2011, 144 (1-3), 113-119.

Preparation of SAPO-35 Molecular Sieve Raw Powder, O35-1:

According to the method described in [Literature 5], a sample was prepared using hexamethyleneimine as the organic templating agent, and after being dried at a temperature of 120° C., a the SAPO-35 molecular sieve raw powder was obtained and denoted as Sample O35-1.

[Literature 5]: *Journal of Physical Chemistry B*, 2005, 109 (44), 20847-20853.

Preparation of SAPO-56 Molecular Sieve Raw Powder, O56-1:

According to the method described in [Literature 6], a sample was prepared using N,N,N,N-tetramethyl-1,6-hexanediamine (abbreviated as TMHD) as the organic templating agent, and after being dried at a temperature of 120° C., a the SAPO-56 molecular sieve raw powder was obtained and denoted as Sample O56-1.

[Literature 6]: *Microporous and Mesoporous Materials*, 1999, 28 (1), 125-137.

Preparation of SAPO-11 molecular sieve raw powder, O11-1:

According to the method described in [Literature 7], a sample was prepared using tetrabutylammonium hydroxide (abbreviated as TBAOH) and di-n-propylamine (abbreviated as $Pr_2NH$) as organic templating agents, and after being dried at a temperature of 120° C., a the SAPO-11 molecular sieve raw powder was obtained and denoted as Sample O11-1.

[Literature 7]: *Topics in Catalysis*, 2008, 49 (3-4), 157-166.

Example 2 Characterization of Molecular Sieve Raw Powder

The molecular sieve raw powder obtained in Example 1 was characterized by X-ray powder diffraction phase analysis. And the results showed that: both O34-1 and O34-2 were SAPO-34 molecular sieve raw powder with a high degree of crystallinity; and O18-1 was SAPO-18 molecular sieve raw powder with a high degree of crystallinity; and O6-1 was DNL-6 molecular sieve raw powder with a high degree of crystallinity; and O35-1 was SAPO-35 molecular sieve raw powder with a high degree of crystallinity; and O56-1 was SAPO-56 molecular sieve raw powder with a high degree of crystallinity; and O11-1 was SAPO-11 molecular sieve raw powder with a high degree of crystallinity.

The molecular sieve powder obtained in Example 1 was characterized by X-ray fluorescence analysis and thermal analysis. The inorganic composition and the organic content of the molecular sieve were shown in Table 1.

Example 3 Preparation of Metal-Modified SAPO Molecular Sieve

The molecular sieve raw powder samples prepared in Example 1 were added to a solution containing metal ions, respectively; and after being stirred for 5 minutes, the mixtures were heated to an ion exchange temperature to ion exchange for a certain time. After being centrifuged and washed for three times with deionized water and dried at 80° C., the metal-modified SAPO molecular sieve samples were obtained.

The corresponding relation between the number of the obtained metal-modified SAPO molecular sieve samples and the number of the molecular sieve raw powders used, the solution containing metal ions, the solid-to-liquid mass ratio of the molecular sieve raw powder to the solution containing metal ions, the ion exchange temperature and time were shown in Table 2.

TABLE 2

| Sample No. | Molecular sieve raw powder No. | Solution containing metal ions Metal salt | Solution concentration and solvent (mol/L) | Solid-to-liquid ratio (g/g) | Ion exchange temperature (° C.) | Ion exchange time (h) |
|---|---|---|---|---|---|---|
| Sample 1 | O34-1 | $Cu(CH_3COO)_2 \cdot H_2O$ | 0.01 (Water) | 1/20 | 50 | 4 |
| Sample 2 | O34-1 | $Cu(CH_3COO)_2 \cdot H_2O$ | 0.01 (Water) | 1/30 | 50 | 4 |
| Sample 3 | O34-1 | $Ni(NO_3)_2 \cdot 6H_2O$ | 0.01 (Water) | 1/30 | 50 | 4 |
| Sample 4 | O34-1 | $Ce(NO_3)_3 \cdot 6H_2O$ | 0.01 (Water) | 1/30 | 50 | 4 |
| Sample 5 | O34-1 | $Mn(CH_3COO)_2 \cdot 5H_2O$ | 0.01 (Water) | 1/30 | 50 | 4 |
| Sample 6 | O56-1 | $Cu(CH_3COO)_2 \cdot H_2O$ | 0.01 (Water) | 1/30 | 50 | 4 |
| Sample 7 | O35-1 | $Cu(CH_3COO)_2 \cdot H_2O$ | 0.01 (Water) | 1/30 | 50 | 4 |
| Sample 8 | O18-1 | $Cu(CH_3COO)_2 \cdot H_2O$ | 0.01 (Water) | 1/30 | 50 | 4 |
| Sample 9 | O11-1 | $Cu(CH_3COO)_2 \cdot H_2O$ | 0.01 (Water) | 1/30 | 50 | 4 |
| Sample 10 | O6-1 | $Cu(CH_3COO)_2 \cdot H_2O$ | 0.01 (Ethanol) | 1/30 | 50 | 4 |
| Sample 11 | O34-1 | $Sr(NO_3)_2$ | 0.01 (Water) | 1/30 | 50 | 4 |
| Sample 12 | O34-1 | $Cu(CH_3COO)_2 \cdot H_2O$ | 0.002 (Water) | 1/100 | 85 | 1 |
| Sample 13 | O34-1 | $Cu(CH_3COO)_2 \cdot H_2O$ | 0.5 (Water) | 1/10 | 30 | 10 |
| Sample 14 | O34-1 | $Cu(CH_3COO)_2 \cdot H_2O$ | 0.01 (Methanol) | 1/8 | 50 | 4 |
| Sample 15 | O34-1 | $Cu(CH_3COO)_2 \cdot H_2O$ | 0.02 (Water) | 1/30 | 50 | 3 |
| Sample 16 | O34-2 | $Cu(CH_3COO)_2 \cdot H_2O$ | 0.01 (Water) | 1/20 | 50 | 4 |

TABLE 1

Composition of molecular sieve raw powder

| Molecular sieve raw powder | Organic templating agent | inorganic composition of molecular sieve | Thermal analysis Exothermic weight loss in 200-600° C. interval (wt %) |
|---|---|---|---|
| O34-1 | Diethylamine | $(Si_{0.2}Al_{0.46}P_{0.34})O_2$ | 10.2% |
| O34-2 | Triethylamine | $(Si_{0.2}Al_{0.46}P_{0.34})O_2$ | 12.1% |
| O18-1 | N,N-diisopropyl-ethylamine | $(Si_{0.22}Al_{0.44}P_{0.34})O_2$ | 11.3% |
| O6-1 | Diethylamine | $(Si_{0.11}Al_{0.54}P_{0.35})O_2$ | 17.9% |
| O35-1 | Hexa-methyleneimine | $(Si_{0.12}Al_{0.51}P_{0.37})O_2$ | 10.3% |
| O56-1 | TMHD | $(Si_{0.22}Al_{0.44}P_{0.34})O_2$ | 11.8% |
| O11-1 | TBAOH and $Pr_2NH$ | $(Si_{0.2}Al_{0.46}P_{0.34})O_2$ | 8.3% |

Comparative Example 1

10 g of the molecular sieve raw powder O34-1 was heated to 600° C. at a rate of 2° C./min and calcined at a constant temperature of 600° C. for 4 hours to remove the organic templating agent and water contained therein.

The calcined SAPO-34 molecular sieve was added to an ammonium nitrate solution with a mass fraction of 27%. After being stirring for 5 minutes, the mixture was heated to 80° C. to ion exchange for 2 hours at 80° C. After being centrifuged and washed for three times with deionized water and dried at 80° C., a $NH_4^+$ type SAPO-34 molecular sieve sample was obtained.

7 g of the $NH_4^+$ type SAPO-34 was added to 210 g of $Cu(CH_3COO)_2$ solution with a concentration of 0.01 mol/L. After being stirred for 5 minutes, the mixture was heated to 50° C. to ion exchange for 4 hours at 50° C. After being centrifuged and washed for three times with deionized water and dried at 80° C., a $NH_4^+$-exchanged Cu-SAPO-34 sample was obtained and denoted as Sample D1.

Comparative Example 2

10 g of the molecular sieve raw powder O56-1 was put into a crucible and evenly spread. Then the crucible was put into a muffle furnace and heated to 600° C. at a rate of 2° C./min. The temperature was maintained at 600° C. for 4 hours to remove the organic templating agent and water contained therein.

The calcined SAPO-56 molecular sieve was added to an ammonium nitrate solution with a mass fraction of 27%. After being stirred for 5 minutes, the mixture was heated to 80° C. to ion exchange for 2 hours at 80° C. After being centrifuged and washed for three times with deionized water and dried at 80° C., a $NH_4^+$ type SAPO-56 molecular sieve sample was obtained.

7 g of the $NH_4^+$ type SAPO-56 was added to 280 g of $Cu(CH_3COO)_2$ solution with a concentration of 0.01 mol/L. After being stirred for 5 minutes, the mixture was heated to 50° C. to ion exchange for 4 hours at 50° C. After being centrifuged and washed for three times with deionized water and dried at 80° C., a $NH_4^+$-exchanged Cu-SAPO-56 sample was obtained and denoted as Sample D2.

Comparative Example 3

Using $Cu(CH_3COO)_2 \cdot H_2O$ as a copper source, an aqueous solution with $Cu(CH_3COO)_2$ concentration of 0.24 mol/L was prepared. Using equal-volume impregnation method, 10 g of the molecular sieve raw powder O34-1 was heterogeneously mixed with 9 ml of the aqueous solution; and after being placed at room temperature for 12 hours and dried at 80° C., a supported Cu/SAPO-34 sample was obtained and denoted as Sample D3.

Example 4 XRD Characterization and Elemental Analysis of Samples 1-16 and D1-D3

Samples 1 to 16 obtained in Example 3 and Samples D1 to D3 obtained in Comparative Examples 1 to 3 were characterized by X-ray powder diffraction phase analysis. The results showed that Samples 1 to 16 obtained in Example 3 all had an XRD diffraction pattern close to that of corresponding molecular sieve raw powder, that is, the peak position of each diffraction peak was the same but the peak intensity was slightly different.

The degree of crystallinity of each sample was shown in Table 3, wherein the degree of crystallinity of each molecular sieve raw powder in Example 2 was regarded as 100%. The degree of crystallinity was calculated according to the equation below:

Degree of crystallinity of a sample=(sum of peak intensities of three strongest diffraction peaks on XRD spectrum of the sample÷sum of peak intensities of corresponding diffraction peaks on XRD spectrum of molecular sieve raw powder)×100%.

Samples 1 to 16 obtained in Example 3 and Samples D1 to D3 obtained in Comparative Examples 1 to 3 were characterized by X-ray fluorescence analysis and CHN element analysis. The mass percentages of metal elements in each sample were shown in Table 3.

TABLE 3

| Sample No. | Degree of crystallinity (%) | Mass percentage of metal element (%) |
| --- | --- | --- |
| Sample 1 | 105 | 1.41 |
| Sample 2 | 97 | 2.08 |
| Sample 3 | 98 | 0.56 |
| Sample 4 | 99 | 2.05 |
| Sample 5 | 96 | 0.75 |

TABLE 3-continued

| Sample No. | Degree of crystallinity (%) | Mass percentage of metal element (%) |
| --- | --- | --- |
| Sample 6 | 103 | 1.75 |
| Sample 7 | 102 | 0.79 |
| Sample 8 | 107 | 0.74 |
| Sample 9 | 101 | 1.07 |
| Sample 10 | 95 | 2.35 |
| Sample 11 | 98 | 0.83 |
| Sample 12 | 96 | 1.46 |
| Sample 13 | 99 | 4.5 |
| Sample 14 | 101 | 0.6 |
| Sample 15 | 104 | 3.93 |
| Sample 16 | 99 | 1.55 |
| Sample D1 | 85 | 1.37 |
| Sample D2 | 83 | 1.85 |
| Sample D3 | 97 | 1.35 |

Example 5

Cu-modified Sample 1, Sample 2, Samples 12 to 16, Sample D1 and Sample D3 were characterized by electron paramagnetic resonance (EPR), respectively. The results showed that except Sample D3, all other samples had similar EPR signals: $Cu^{2+}$ ions in the samples possessed symmetry and coordinated with three framework oxygen atoms and three water molecules, and all of $Cu^{2+}$ ions were located at ion sites close to the double six-membered ring in oval cages. In Sample D3, the EPR signal of $Cu^{2+}$ was much weaker than D1 when the sample loading amount was the same, indicating that most copper element was not located at ion sites.

For Samples 6 to 10 and Sample D2, the state of copper species was characterized by $H_2$-TPR. The results showed that the reduction peak of CuO species was small and the reduction peak of $Cu^{2+}$ was larger, indicating that the exchanged copper were mostly located at ion sites. Sample D2 and Sample 6 had similar peak shape, peak area and peak position, indicating that the samples obtained by two catalyst preparation methods had a similar metal distribution.

Example 6

The distribution of copper ions in SAPO-34 crystal grains of Sample 1 and Sample D1 was determined by EDX element line scan. The SAPO-34 crystal were cubic with a size (from one angle of quadrilateral to corresponding opposite angle) of about 5 microns. It was found that in Sample 1 and Sample D1 the element distribution of copper ions in the crystal was similar, which showed the effectiveness of the ion exchange performed on the SAPO raw powder and also indicated that the presence of the templating agent in SAPO molecular sieve raw powder had no significant effect on the diffusion of Cu ions during the ion exchange procedure.

Example 7 Evaluation of Performance in a $NO_x$ Removal Reaction

Sample 1, Sample D1 and Sample D3 were calcined at 650° C. for 2 hours, respectively. After removal of the templating agent, the obtained samples were denoted as Sample A, Sample B and Sample C, respectively. The catalytic performance for selectively reduction of $NO_x$ with $NH_3$ of Sample A, Sample B and Sample C were tested respectively. The specific experimental process and conditions were as follows: after being calcined, the sample was pressed and sieved; 0.1 g of sample (60-80 mesh) and 0.4 g of quartz sand (60-80 mesh) were weighted, mixed and loaded into a fixed bed reactor. After being activated at 600° C. under nitrogen for 40 min, the temperature was reduced to 120° C. and start the reaction, and then the temperature was programmed heating to 550° C.

The feed gas consist of: NO, 500 ppm; $NH_3$, 500 ppm; $O_2$, 5%; and $H_2O$, 5%. The gas flow rate was 300 ml/min.

The reaction product was analyzed using a Bruker's Tensor 27 instrument for online FTIR analysis. The changes of NO Conversion with Temperature on Sample A, Sample B and Sample C were shown in FIG. 1.

It can be seen from FIG. 1 that Sample A had good reaction activity, which could achieve an almost equivalent reactivity with Sample B when its copper content was slightly lower than Sample B. It should be related to the good maintenance of the framework structure during the ion exchange process of the SAPO-34 raw powder. The Sample C prepared by the impregnation method was less reactive because of the fact that copper ions were not located at ion sites, and the side reactions at high temperature were more serious.

Example 8 Evaluation of Performance in a Methanol to Olefins Reaction

Sample 11 and the molecular sieve raw powder O34-1 were calcined at 600° C. under air for 4 hours, and then compressed and crushed to 20-40 mesh to obtain catalyst samples, respectively. The catalyst samples were used as the catalysts for methanol to olefins (MTO) reaction, respectively. Respectively, 0.3 g of the catalyst samples were loaded into a fixed bed reactor, activated at 550° C. for 1 hour under nitrogen, and then cooled to 450° C. to perform the reaction. Methanol was carried by nitrogen, with a nitrogen flow rate of 40 ml/min and a methanol WHSV of 2.0 $h^{-1}$. The reaction product was analyzed by on-line gas chromatography. The results of the reaction were shown in Table 4.

TABLE 4

Results of methanol to olefins reaction

| Sample | Life (min) | Selectivity (weight %)* | | | | | | | |
| --- | --- | --- | --- | --- | --- | --- | --- | --- | --- |
| | | $CH_4$ | $C_2H_4$ | $C_2H_6$ | $C_3H_6$ | $C_3H_8$ | $C_4^+$ | $C_5^+$ | $C_2H_4 + C_3H_6$ |
| Sample 11 | 200 | 2.56 | 52.76 | 0.25 | 31.29 | 0.21 | 7.73 | 5.20 | 84.05 |
| SAPO-34 | 150 | 2.62 | 51.76 | 0.25 | 30.88 | 0.40 | 9.02 | 5.07 | 82.64 |

*The highest selectivity for (ethylene + propylene) when the methanol conversion was 100%.

While the present application has been described above with reference to preferred embodiments, but these embodiments are not intended to limit the claims. Without departing from the spirit of the present application, people skilled in the art will be able to make several possible variations and modifications and thus the protection scope shall be determined by the scope as defined in the claims.

The invention claimed is:

1. A preparation method for a metal-modified SAPO molecular sieve, which comprises at least the following steps:

adding SAPO molecular sieve raw powder to a solution containing metal ions and performing ion exchange, and then washing and drying the obtained solid after the ion exchange, so as to obtain the metal-modified SAPO molecular sieve wherein the molecular sieve raw powder has not been calcined at a temperature above 300° C., and an organic templating agent and water are contained in channels and cages of the molecular sieve raw powder;

wherein the metal ion is at least one selected from Group IA metal ions, Group IIA metal ions, Group IIIA metal ions, Group VA metal ions, Group IVB metal ions, Group VB metal ions, Group VIIB metal ions, Group VIII metal ions, Group IB metal ions, lanthanide metal ions, and wherein there are no steps of calcining the molecular sieve raw powder and ammonium exchange in the method; wherein metal ions are located at ion sites in channels and/or cages of the metal-modified SAPO molecular sieve; the mass ratio of the SAPO molecular sieve raw powder to the solution containing metal ions is in a range from 1:8 to 1:100, the metal ion concentration in the solution containing metal ions is in a range from 0.005 mol/L to 0.5 mol/L; the ion exchange temperature is in a range from 40° C. to 90° C., and the ion exchange time is in a range from 0.5 h to 10 h.

2. The method according to claim 1, wherein the SAPO molecular sieve raw powder is at least one selected from SAPO-34 molecular sieve raw powder, SAPO-35 molecular sieve raw powder, SAPO-56 molecular sieve raw powder, SAPO-18 molecular sieve raw powder, SAPO-5 molecular sieve raw powder, SAPO-11 molecular sieve raw powder, DNL-6 molecular sieve raw powder.

3. The method according to claim 1, wherein the metal ion is at least one selected from copper ions, iron ions, lanthanum ions, cerium ions, cobalt ions, nickel ions, manganese ions, magnesium ions, vanadium ions, zirconium ions, barium ions, platinum ions, gold ions, palladium ions, silver ions, rhodium ions, ruthenium ions, aluminum ions, bismuth ions, gallium ions, calcium ions, strontium ions, lithium ions, sodium ions, potassium ions, rubidium ions, cesium ions.

4. The method according to claim 1, wherein an organic templating agent is used in the synthesis of the SAPO molecular sieve raw powder.

5. The method according to claim 4, wherein the organic templating agent used in the synthesis of the SAPO-34 molecular sieve raw powder contains at least one organic amine compound with no more than 8 carbon atoms; the organic templating agent used in the synthesis of SAPO-18 molecular sieve raw powder contains at least one organic amine compound with no more than 8 carbon atoms; the organic templating agent used in the synthesis of SAPO-56 molecular sieve raw powder contains at least one organic amine compound with no more than 10 carbon atoms; the organic templating agent used in the synthesis of SAPO-5 molecular sieve raw powder contains at least one organic amine compound with no more than 9 carbon atoms; the organic templating agent used in the synthesis of SAPO-11 molecular sieve raw powder contains at least one organic amine compound with no more than 8 carbon atoms; the organic templating agent used in the synthesis of SAPO-35 molecular sieve raw powder contains at least one organic amine compound with no more than 8 carbon atoms; and the organic templating agent used in the synthesis of DNL-6 molecular sieve raw powder contains at least one organic amine compound having no more than 8 carbon atoms.

6. The method according to claim 1, wherein the obtained solid is washed, dried and calcined at a temperature no less than 600° C., to obtain the metal-modified SAPO molecular sieve.

* * * * *